United States Patent [19]

Eizember et al.

[11] 4,185,035

[45] Jan. 22, 1980

[54] DINITROANILINE PURIFICATION WITH INORGANIC ACID HALIDES

[75] Inventors: Richard F. Eizember, Greenwood; Kathleen R. Vogler, Indianapolis, both of Ind.

[73] Assignee: Eli Lilly and Company, Indianapolis, Ind.

[21] Appl. No.: 878,843

[22] Filed: Feb. 17, 1978

Related U.S. Application Data

[63] Continuation-in-part of Ser. No. 830,261, Sep. 2, 1977, abandoned.

[51] Int. Cl.$^2$ .................... C07C 85/24; C07C 85/26; C07C 143/80
[52] U.S. Cl. ...................................... 260/577; 71/121; 260/397.7 R; 260/647; 260/583 CC; 260/397.6
[58] Field of Search ........ 260/577, 578, 582, 583 CC, 260/647, 397.7 R, 556 B; 71/121

[56] References Cited

FOREIGN PATENT DOCUMENTS 482795  9/1929  Fed. Rep. of Germany ........... 260/582
2035796 1/1972  Fed. Rep. of Germany ........... 260/577

OTHER PUBLICATIONS

Biggs et al., "J. Chem. Soc., Perkin Trans. II," pp. 107–111 (1975).
Biggs et al., "J. Chem. Soc., Perkin Trans. II," pp. 601–605 (1976).
Lunt et al., "Anal. Lett.," 6(4), pp. 369–372 (1973).
Fridman et al., "Russian Chem. Rev.", 40(1), pp. 34–50 (1971).
Smith, "The Chem. of Open-Chain Org. Nitrogen Cmpds.," pp. 470–474 (1966).
Sidgwick, "The Org. Chem. of Nitrogen," pp. 592–594 (1966).

Primary Examiner—Winston A. Douglas
Assistant Examiner—John Doll
Attorney, Agent, or Firm—Kathleen R. S. Page; Arthur R. Whale

[57] ABSTRACT

The present invention is directed to a process for reducing the concentration of nitrosamines in dinitroanilines, which comprises treating a nitrosamine-containing dinitroaniline with $PCl_3$, $PCl_5$, $PBr_3$, $POCl_3$, $SCl_2$, $SOCl_2$, $SO_2Cl_2$, $SOBr_2$, or $TiCl_4$.

18 Claims, No Drawings

DINITROANILINE PURIFICATION WITH INORGANIC ACID HALIDES

CROSS REFERENCE TO RELATED APPLICATION

This is a continuation-in-part of our copending application Ser. No. 830,261, filed Sept. 2, 1977, and abandoned after the filing of this application.

SUMMARY

The dinitroaniline class of compounds includes numerous commercial herbicides. Recently a new analytical device, known as a thermal energy analyzer (TEA), has been developed (*J. Chromatogr.* 107 (1975), 351 and references there cited; and "N-Nitroso Compounds in the Environment," IARC Scientific Publication #9 (International Agency for Research on Cancer, Lyon, 1974), p. 40). The TEA analyzes specifically for the nitroso (—NO) group, and is capable of detecting the nitroso group at concentrations as low as 0.02 ppm—much lower than prior analytical techniques. Analysis of various dinitroanilines by the TEA reveals that some of the dinitroanilines contain very small amounts of nitrosamines. Certain of the nitrosamines have been shown to be carcinogenic in animals. Therefore, it is desirable to reduce the concentration of nitrosamines in the dinitroanilines.

DETAILED DESCRIPTION

The present invention is directed to a process which comprises
(1) contacting a nitrosamine-containing dinitroaniline selected from the group consisting of
  trifluralin,
  isopropalin,
  benefin,
  ethalfluralin,
  butralin,
  tendimethalin,
  fluchloralin,
  profluralin,
  dinitramine,
  4-trifluoromethyl-2,6-dinitro-3-chloro-N,N-diethylaniline,
  4-methyl-2,6-dinitro-N,N-bis(2-chloroethyl)aniline,
  oryzalin, and
  nitralin,
  (a) in liquid phase,
  (b) with a reagent selected from the group consisting of $PCl_3$, $PCl_5$, $PBr_3$, $POCl_3$, $SCl_2$, $SOCl_2$, $SO_2Cl_2$, $SOBr_2$, and $TiCl_4$, until the concentration of the nitrosamine has been reduced, and
(2) thereafter recovering the dinitroaniline.

Dinitroanilines with which the present invention can be practiced (and their generic names where available) are
(1) 4-trifluoromethyl-2,6-dinitro-N,N-di-n-propylaniline (trifluralin);
(2) 4-isopropyl-2,6-dinitro-N,N-di-n-propylaniline (isopropalin);
(3) 4-trifluoromethyl-2,6-dinitro-N-n-butyl-N-ethylaniline (benefin);
(4) 4-trifluoromethyl-2,6-dinitro-N-ethyl-N-methallylaniline (ethalfluralin);
(5) 4-tert-butyl-2,6-dinitro-N-sec-butylaniline (butralin);
(6) 3,4-dimethyl-2,6-dinitro-N-(1-ethylpropyl)aniline (tendimethalin);
(7) 4-trifluoromethyl-2,6-dinitro-N-propyl-N-(2-chloroethyl)aniline (fluchloralin);
(8) 4-trifluoromethyl-2,6-dinitro-N-propyl-N-(cyclopropylmethyl)aniline (profluralin);
(9) 4-trifluoromethyl-2,6-dinitro-3-amino-N,N-diethylaniline (dinitramine);
(10) 4-trifluoromethyl-2,6-dinitro-3-chloro-N,N-diethylaniline (intermediate to dinitramine);
(11) 4-methyl-2,6-dinitro-N,N-bis(2-chloroethyl)aniline;
(12) 4-sulfamoyl-2,6-dinitro-N,N-di-n-propylaniline (oryzalin); and
(13) 4-(methylsulfonyl)-2,6-dinitro-N,N-di-n-propylaniline (nitralin).

Preferred dinitroanilines with which the present invention is carried out are trifluralin, isopropalin, benefin, and ethalfluralin.

Generally, the dinitroanilines are prepared by a reaction route of which the following, for trifluralin, is typical:

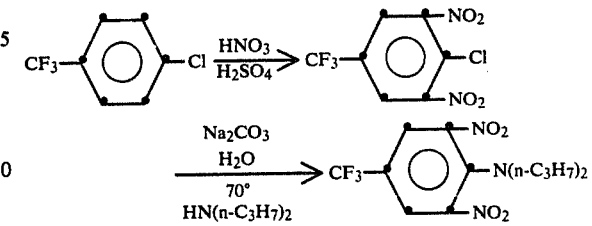

It is believed that small amounts of nitrogen oxides remaining from the nitration step react with a portion of the amine during the amination step, generating small amounts of nitrosamine which may appear in the final dinitroaniline product. Therefore, any nitrosamine contaminant is expected to be the nitroso derivative of the alkylamine employed. However, it is conjectured that exceedingly small amounts of yet other nitrosamines may also be formed. The removal of nitrosamines, regardless of identity, is desirable, and the present process meets that objective.

The mechanism by which the present process operates is not known with certainty. It is known, however, that the nitrosamine is converted, "denitrosated," to a substance not containing the nitrosamine group. The present process provides substantial reduction in nitrosamine concentration, regardless of the initial amount of nitrosamine. In most cases, the nitrosamine concentration is reduced to less than about 10 ppm.

The present process is conducted in a liquid phase. In the case of those dinitroanilines melting at lower temperatures, such as below about 140° C., this is preferably achieved by heating the nitrosamine-containing dinitroaniline to its melting temperature or somewhat higher. Trifluralin melts at about 54°–5° C., benefin, at about 65°–6° C., and ethalfluralin, at about 57°–9° C. Isopropalin melts at about 30° C. but because of minor impurities is generally liquid at room temperatures. Additionally, a liquid phase can be achieved by dissolving the nitrosamine-containing dinitroaniline in a solvent. Suitable solvents include aromatic solvents such as benzene and toluene; and halogenated aliphatic hydrocarbons, such as chloroform, methylene chloride, and carbon tetrachloride.

The amount of reagent to be employed is not critical, so long as the amount is sufficient to reduce the initial amount of nitrosamine to a lesser amount. In general, 0.1 to 2.0 grams of reagent per 100 grams of dinitroaniline is satisfactory.

The reaction can be conducted at temperatures over a wide range, such as from room temperature to about 140° C. When conducting the process neat, the reaction is conducted at temperatures above the melting temperature of the particular dinitroaniline. Good results have been obtained at temperatures of from 70° to 90° C. when conducting the process neat with trifluralin, isopropalin, benefin, and ethalfluralin. The reaction can be conducted at atmospheric pressure or at elevated pressures.

The rate at which the present process proceeds will vary with the concentration of the nitrosamine, temperature, the reagent, the rate of its addition, and other factors. The presence of water is deleterious. The progress of nitrosamine removal can be monitored by gas chromatography or by TEA analysis. Denitrosation is generally complete in less than an hour. Time studies of the present process have shown an early drop in levels of nitrosamine, followed in some instances by a slight rise in levels of nitrosamine upon extended reaction time. It is believed that extended exposure of (1) the dinitroaniline and (2) the denitrosation products, to the reaction conditions may result in further nitrosamine formation. Therefore, minimizing reaction times is desirable.

Workup desirably takes the form of neutralization and separation of the purified dinitroaniline.

The following examples illustrate the present invention and will enable those skilled in the art to practice the invention.

Unless otherwise noted, determination of nitrosamine concentration in the following examples was done by a gas chromatographic method sensitive down to about 0.5 ppm. A "non-detectable" reading (reported below as "N.D.") was considered to represent less than about 0.5 ppm of nitrosamine. A Hewlett-Packard Model 5711A gas chromatograph was used but the method can be carried out with any gas chromatograph apparatus equipped with a flame ionization detector. The column was a glass coil 4 ft.×⅛ inch i.d., packed with 3% Carbowax 20M on 100/120 mesh AW DMCS Chromosorb G operated at 100° C. After the nitrosamine peak eluted, the column was heated to 230° C. and held there for about 15 minutes. The helium flow rate was 60 ml/min. A standard of approximately the same concentration of the nitrosamine expected in the sample was employed. Both standard and sample were prepared in methylene chloride.

Those examples utilizing TEA analysis are so indicated. Analyses by this method were carried out in essentially the same procedures as described at *J. Chromatogr.* 109 (1975), 271. In the context of the present invention, this method is considered to be sensitive to nitrosamine concentrations as low as about 0.05 ppm. Where TEA analysis of the samples reported below showed no nitrosamine, it is reported as "N.D."

EXAMPLE 1

NITROSAMINE REMOVAL FROM TRIFLURALIN, $PCl_3$

A 30-gram portion of a lot of trifluralin with an average assay of 68 ppm of nitrosamine and 0.5 gram of $PCl_3$ were mixed and heated to 70° C. The reaction mixture was maintained at 70° C., with stirring, for one hour. Samples were taken at 30 minutes and 1 hour and analyzed for nitrosamine concentration. Thereafter, the reaction mixture was neutralized with 2 ml of 10% sodium carbonate solution, the layers were separated, and the aqueous layer was extracted with an equal amount of methylene chloride. The methylene chloride extract was also analyzed for nitrosamine content. The results were as follows:

| Time when Sample taken | Nitrosamine Concentration |
| --- | --- |
| 30 min. | 1.2 ppm |
| 1 hour | N.D. |
| -(methylene chloride extract) | N.D. |

EXAMPLE 2

NITROSAMINE REMOVAL FROM TRIFLURALIN, $PCl_3$

The reaction reported in Example 1 was repeated except that (1) only 0.2 gram of $PCl_3$ was used; (2) the temperature was 90° C.; and (3) the reaction was terminated at 30 minutes. A sample was analyzed for nitrosamine content and 0.9 ppm was detected.

EXAMPLE 3

NITROSAMINE REMOVAL FROM TRIFLURALIN, $PCl_3$

The reaction reported in Example 2 was repeated except that only 0.02 gram of $PCl_3$ was used. A sample was analyzed for nitrosamine content; none was detected.

EXAMPLE 4

NITROSAMINE REMOVAL FROM TRIFLURALIN, $PCl_3$

The reaction reported in Example 3 was repeated except that the temperature was 120° C. Analysis of a sample showed no nitrosamine.

EXAMPLE 5

NITROSAMINE REMOVAL FROM ETHALFLURALIN, $PCl_3$

A 30 gram sample of ethalfluralin with a nitrosamine assay of 8.6 ppm was heated to 90° C., 0.2 gram of $PCl_3$ was added, and the reaction mixture was stirred for 1 hour at 90° C. A 10% sodium carbonate solution (5 ml) was added and the layers separated. A sample of the ethalfluralin layer was taken and analyzed for nitrosamine content by TEA; the analysis showed 5 ppm of nitrosamine.

EXAMPLE 6

NITROSAMINE REMOVAL FROM ISOPROPALIN, $PCl_3$

A xylene solution of isopropalin (50 ml, representing 35 grams of isopropalin with a nitrosamine assay of 33.5 ppm) was stripped on a rotary evaporator for 20 minutes at 90° C. $PCl_3$ (0.5 ml) was added and the reaction mixture stirred at 80° C. for 30 minutes. A 5% sodium carbonate solution (20 ml) was added and the mixture stirred for 10 minutes, then stripped on a rotary evaporator (15 minutes at 100° C.) and analyzed for nitrosamine content. The analysis showed 1.9 ppm of nitrosamine.

EXAMPLES 7–9

NITROSAMINE REMOVAL FROM TRIFLURALIN, SOCL₂

A series of three reactions was conducted, varying the amount of SOCl₂ employed, the reaction temperature, and the reaction time. In each reaction, the SOCL₂ and a 30 gram portion of a lot of trifluralin with an average assay of 68 ppm of nitrosamine were mixed and heated to the reaction temperature. The reaction mixture was maintained at that temperature for the specified period, then neutralized with 2 ml of 10% sodium carbonate solution. The layers were separated and in the first reaction of the series, the organic layer was extracted with an equal amount of methylene chloride. Samples were analyzed for nitrosamine content with the following results.

|  | Amount of SOCl₂ | Reaction Temperature | Time when Sample taken | Nitrosamine Concentration |
|---|---|---|---|---|
| Ex. 7 | 0.5 g | 70° C. | 30 min. | 22 ppm |
|  |  |  | 1 hour | 11 " |
|  |  |  | methylene chloride extract | 0.7 μg/ml |
| Ex. 8 | 0.2 g | 90° C. | 30 min. | 3.9 ppm |
| Ex. 9 | 0.1 g | 120° C. | 30 min. | 3.2 " |

EXAMPLE 10

NITROSAMINE REMOVAL FROM ETHALFLURALIN, SOCL₂

A 30 gram sample of ethalfluralin with an assay of 8.6 ppm of nitrosamine was heated to 90° C., 0.2 gram of SOCl₂ was added, and the reaction mixture was stirred at 90° C. for an hour. A 10% sodium carbonate solution (5 ml) was added and the layers were separated. Analysis of the organic layer by TEA showed 0.44 ppm of nitrosamine.

EXAMPLES 11–13

NITROSAMINE REMOVAL FROM TRIFLURALIN, PBR₃

In a first reaction, a 30 gram portion of a lot of trifluralin with an average assay of 68 ppm of nitrosamine was heated to 70° C. and 0.5 gram of PBr₃ was added. The reaction mixture was maintained at 70° C. for 30 minutes, then neutralized with dilute sodium carbonate solution and the layers separated. The organic layer was analyzed for nitrosamine and showed 1.1 ppm.

The reaction was repeated under essentially the same conditions except that the reaction temperature was 90° C. and only 0.1 gram of PBr₃ was used. Nitrosamine concentration was reduced to 2.3 ppm.

The reaction was carried out again under essentially the same conditions, except that the reaction temperature was 120° C. and the amount of PBr₃ was 0.1 gram. Assay for nitrosamine showed none detectable.

EXAMPLE 14

NITROSAMINE REMOVAL FROM TRIFLURALIN, TICL₄

A 30 gram portion of a lot of trifluralin with an average assay of 68 ppm was heated to 90° C. and 0.1 ml of TiCl₄ added. The reaction mixture was maintained at 90° C. and samples periodically removed and analyzed without workup for nitrosamine content. Results were as follows.

| Time when Sample taken | Nitrosamine Concentration |  |
|---|---|---|
| 15 min. | 59 | ppm |
| 30 min. | 16 | " |
| 1 hour | 21 | " |
| 2 hours | 3.8 | " |

EXAMPLE 15

NITROSAMINE REMOVAL FROM TRIFLURALIN, SULFUR DICHLORIDE

To 100 grams of molten trifluralin, 0.2 gram of sulfur dichloride was added, and the reaction mixture was stirred for one hour at 90° C. Samples were removed and analyzed for nitrosamine without workup. The results were as follows:

| Time when Sample taken | Nitrosamine Concentration |  |
|---|---|---|
| 0 | 50 | ppm |
| 30 min. | 7.4 | " |
| 1 hour | 7.3 | " |

EXAMPLES 16–18

NITROSAMINE REMOVAL FROM TRIFLURALIN, POCL₃

Three reactions were conducted with POCl₃. In each, a 30 gram portion of a lot of trifluralin with an average assay of 68 ppm of nitrosamine was heated to a reaction temperature, an amount of POCl₃ was added, and the reaction mixture was maintained for 30 minutes at the reaction temperature. The reaction mixture was neutralized with sodium carbonate and a sample of the organic layer analyzed for nitrosamine. The reaction conditions and results were as follows.

| Amount of POCl₃ | Reaction Temperature | Nitrosamine Concentration |
|---|---|---|
| 0.5 g | 70° C. | 5 ppm |
| 0.1 g | 90° C. | 10 ppm |
| 0.1 g | 120° C. | 14 ppm |

EXAMPLE 19

NITROSAMINE REMOVAL FROM TRIFLURALIN, PCL₃, EFFECT OF BASE

A 30 gram portion of a lot of trifluralin with an average nitrosamine assay of 68 ppm was mixed with 0.2 gram of PCl₃ and 0.05 gram of sodium carbonate. The reaction mixture was heated to 90° C. and maintained at 90° C. for 30 minutes, then neutralized with 2 ml of 10% sodium carbonate solution and the layers separated. A sample of the trifluralin layer was then analyzed for nitrosamine content; none was detected.

EXAMPLE 20

NITROSAMINE REMOVAL FROM TRIFLURALIN, PCL₃, TIME STUDIES

A 30 gram portion of a lot of trifluralin with an average nitrosamine assay of 68 ppm was heated to 90° C. and PCl₃ (0.03 ml) was added. The reaction mixture was maintained at 90° C. for two hours with samples taken periodically and analyzed. Results were as follows:

| Time when sample taken | Nitrosamine Concentration |
| --- | --- |
| 15 min. | 6.6 ppm |
| 30 min. | <1 ppm |
| 1 hour | 4.9 ppm |
| 2 hours | 8.5 ppm |

EXAMPLE 21

NITROSAMINE REMOVAL FROM TRIFLURALIN, SO₂CL₂

A 30 ml. portion of trifluralin with a nitrosamine assay of 36 ppm was heated to 120° C. and 0.5 ml of SO₂Cl₂ was added. The reaction mixture was maintained at 120° C. for 1 hour. Samples were taken at 30 minutes and 1 hour. Each sample was washed with 10 ml of water, dried on a rotary evaporator for 15 minutes at 60° C., and analyzed for nitrosamine content. Results were as follows:

| Time when Sample taken | Nitrosamine Concentration |
| --- | --- |
| 30 min. | 4 |
| 1 hour | 2 |

EXAMPLE 22

NITROSAMINE REMOVAL FROM TRIFLURALIN, PCL₅

The reaction reported on Example 21 was repeated except that PCl₅ (0.5 gram) was employed instead of SO₂Cl₂. Results were as follows:

| Time when Sample taken | Nitrosamine Concentration |
| --- | --- |
| 30 min. | 8 |
| 1 hour | 4 |

We claim:
1. The process which comprises
   (1) contacting a nitrosamine-containing dinitroaniline selected from the group consisting of
       trifluralin,
       isopropalin,
       benefin,
       ethalfluralin,
       butralin,
       tendimethalin,
       fluchloralin,
       profluralin,
       dinitramine,
       4-trifluoromethyl-2,6-dinitro-3-chloro-N,N-diethylaniline,
       4-methyl-2,6-dinitro-N,N-bis(2-chloroethyl)aniline,
       oryzalin, and
       nitralin,
       (a) in liquid phase,
       (b) with a reagent selected from the group consisting of PCl₃, PCl₅, PBr₃, and POCl₃, until the concentration of the nitrosamine has been reduced, and
   (2) thereafter recovering the dinitroaniline.
2. The process of claim 1 in which the dinitroaniline is trifluralin, isopropalin, benefin, or ethalfluralin.
3. The process of claim 2 in which the dinitroaniline is trifluralin.
4. The process of claim 2 in which the dinitroaniline is isopropalin.
5. The process of claim 2 in which the dinitroaniline is benefin.
6. The process of claim 2 in which the dinitroaniline is ethalfluralin.
7. The process of claim 2 in which the reagent is PCl₃.
8. The process of claim 7 conducted neat at temperatures of 70°–90° C.
9. The process of claim 8 in which the dinitroaniline is trifluralin.
10. The process of claim 8 in which the dinitroaniline is isopropalin.
11. The process of claim 8 in which the dinitroaniline is benefin.
12. The process of claim 8 in which the dinitroaniline is ethalfluralin.
13. The process of claim 1 in which the dinitroaniline is butralin.
14. The process of claim 1 in which the dinitroaniline is tendimethalin.
15. The process of claim 1 in which the dinitroaniline is fluchloralin.
16. The process of claim 1 in which the dinitroaniline is profluralin.
17. The process of claim 1 in which the dinitroaniline is dinitramine.
18. The process of claim 1 in which the dinitroaniline is 4-trifluoromethyl-2,6-dinitro-3-chloro-N,N-diethylaniline.

* * * * *